(12) United States Patent
Ruskin (10) Patent No.: US 6,821,928 B2
(45) Date of Patent: Nov. 23, 2004

(54) METHOD TO REDUCE THE RATE OF DIFFUSION OF SLOW-RELEASE MATERIALS THROUGH POLYMERS AND PROCESS FOR MAKING DRIP IRRIGATION DEVICES WITH LONG-TERM CONTROL OF ROOT GROWTH

(76) Inventor: Rodney Ruskin, 50 Pemberton Pl., San Francisco, CA (US) 94114

( * ) Notice: Subject to any disclaimer, the term of this patent is extended or adjusted under 35 U.S.C. 154(b) by 0 days.

(21) Appl. No.: 10/284,862

(22) Filed: Oct. 31, 2002

(65) Prior Publication Data

US 2003/0092817 A1 May 15, 2003

Related U.S. Application Data

(60) Provisional application No. 60/332,952, filed on Nov. 6, 2001.

(51) Int. Cl.$^7$ .......................... A01N 25/08; A01N 33/18
(52) U.S. Cl. ...................... 504/347; 504/367; 514/949; 514/964; 514/965
(58) Field of Search ............................... 504/347, 367; 514/949, 964, 965

(56) References Cited

U.S. PATENT DOCUMENTS

| 2,918,394 | A |   | 12/1959 | Smith |
|---|---|---|---|---|
| 3,370,115 | A |   | 2/1968 | Wood |
| 3,884,269 | A |   | 5/1975 | Schetty et al. |
| 4,037,791 | A |   | 7/1977 | Mullett et al. |
| 4,168,799 | A | * | 9/1979 | Turner ......................... 239/145 |
| 4,702,787 | A |   | 10/1987 | Ruskin et al. |
| 4,800,109 | A |   | 1/1989 | Washizu |
| 4,889,885 | A |   | 12/1989 | Usuki et al. |
| 4,948,295 | A |   | 8/1990 | Pramsoler |
| 5,052,625 | A |   | 10/1991 | Ruskin |
| 5,111,996 | A |   | 5/1992 | Eckstein |
| 5,116,414 | A |   | 5/1992 | Burton et al. |
| 5,141,360 | A |   | 8/1992 | Zeman |
| 5,152,634 | A |   | 10/1992 | Maso |
| 5,164,460 | A |   | 11/1992 | Yano et al. |
| 5,192,027 | A |   | 3/1993 | Delmer et al. |
| 5,332,160 | A |   | 7/1994 | Ruskin |
| 6,057,396 | A |   | 5/2000 | Lan et al. |
| 6,262,162 | B1 |  | 7/2001 | Lan et al. |
| 2002/0115777 | A1 |  | 8/2002 | Wu et al. |

FOREIGN PATENT DOCUMENTS

| DE | 2742912 A1 | 3/1979 |
|---|---|---|
| EP | 0548940 A1 | 6/1993 |
| EP | 0636315 A1 | 2/1995 |
| GB | 2174884 A | 11/1986 |
| WO | WO 88/01200 A1 | 2/1988 |
| ZA | 861133 | 9/1986 |

OTHER PUBLICATIONS

European Patent Office, "PCT International Preliminary Examination Report," International Application No. PCT/US02/35183; Applicant: Ruskin, Rodney; Dated Jan. 21, 2004.
Internet Paper: http://www.appchem.waseda.ac.jp/inorg/interc.html, KS Lab Res. Int. Intercalation, Preparation of inorganic nanocomposites by intercalation and its application to materials. 2 pages, Jun. 1999.
Internet Paper: http://geoflow.com/wastewater/sdi.html, I.A. paper 1992, Reprinted from *Management of Irrigation and Drainage Systems Integrated Perspectives*, Ruskin, Rodney, "Subsurface Drip Irrigation Can Reduce Pollution," 8 pages.
Internet Paper: http://geoflow.com/rootguard/protectionofburied.html, Van Voris, P. et al., "Protection of Buried Drip Irrigation Devices From Root Intrusion Through Slow–Release Herbicides" 5 pages, 1988.
Sherman, Lilli Manolis, *Plastics Technology Online*, "Nanocomposites A Little Goes A Long Way," Jun. 1999, 5 pages.
Harber, Richard A. et al. "Overview of Traditional Ceramics," *Introduction to Ceramics and Glasses*, (undated) 6 pgs.
Internet Paper: http://geoflow.com/rootguard/cleanwatercont.htm, retrieved on Jun. 29, 1999, "Treflan and Your Water," 4 pgs.
Internet Paper: http://geoflow.com/rootguard/battelle.htm, retrieved on Jun. 29, 1999, "Biobarrier Protection for Buried Drip Irrigation Systems," 3 pgs.

* cited by examiner

*Primary Examiner*—S. Mark Clardy
(74) *Attorney, Agent, or Firm*—Christie, Parker & Hale, LLP (57) ABSTRACT

A method for reducing the rate of diffusion of a slow-release material through a host polymer material to increase the useful life of a slow-release product. An inert fine particulate inorganic material such as an intercalation material having a layered structure is incorporated into a mixture of the slow-release material and the host polymer. The intercalation material has its layers intercalated with molecules of the slow-release material which are accommodated within spaces between the layers of the intercalation material. The particulate material slows the diffusion rate of the slow-release material through the host polymer when compared with the diffusion rate of the same slow-release material through the same host polymer not containing the particulate material. In one embodiment, the intercalation material comprises a nano-clay, the host polymer is a polyolefin, and the slow-release material is a bioactive material such as dinitroanaline. The slow-release product can comprise a drip irrigation emitter device or tube or tape or device used adjacent to an emitter to protect against root intrusion. The intercalation material can comprise a layered nano-clay produced by contacting the clay with a surface modifier to achieve sorption and complexing of the surface modifier between adjacent spaced layers of the clay material, sufficient to expand the spacing between adjacent platelets. This is followed by exfoliating the surface-treated material to separate the platelets, followed by mixing the exfoliated platelets with the polymeric material to form a polymeric matrix from which drip irrigation products can be made.

35 Claims, 6 Drawing Sheets

METHOD TO REDUCE THE RATE OF DIFFUSION OF SLOW-RELEASE MATERIALS THROUGH POLYMERS AND PROCESS FOR MAKING DRIP IRRIGATION DEVICES WITH LONG-TERM CONTROL OF ROOT GROWTH

CROSS-REFERENCE TO RELATED APPLICATION

This application claims priority to U.S. Provisional Application No. 60/332,952, filed Nov. 6, 2001, which is incorporated herein by this reference.

FIELD OF THE INVENTION

This invention relates to "slow-release" materials and to a process for controlling the diffusion rate at which a slow-release material diffuses from a substrate or carrier. One application of the invention is for drip irrigation, and more particularly, drip irrigation devices having a controlled release rate of a herbicide that inhibits root growth. The invention extends the useful life of the drip irrigation product.

BACKGROUND OF THE INVENTION

There are products in the marketplace which depend upon slow-release technology. An example is described in U.S. Pat. No. 5,116,414 to Burton et al. in which trifluralin (also referred to herein by the name Treflan, a trademark of Dow Agrosciences) is slowly released from a polymer into soil to inhibit root intrusion into that area. Another example is flea repellent dog collars where an insecticide is slowly released from the polymer in the collar. There are examples of slow-release or "sustained release" systems for other insecticides as well. A further example is South African Patent No. 86/1133 to Ruskin in which trifluralin is slowly released from a buried drip irrigation device in order to inhibit root intrusion into the device. (The Burton et al. and Ruskin patents are incorporated herein by this reference.)

In many cases more of the active material is released than is needed to efficiently meet the product requirements, whereas a lower rate of diffusion through the polymer would result in a longer product life. For instance, the active sustained release material, such as an insecticide, may be volatile and diffuse from the carrier device too rapidly, shortening retention life. A shortened retention life also can be a problem in the area of drip irrigation.

More specifically, drip irrigation devices which are often used in buried applications inhibit root intrusion by incorporating a herbicide such as trifluralin into the in-line drip emitter. Experience has shown success in protection of such buried drip irrigation devices from root penetration lasting for periods of many years. In addition to incorporating the Treflan (or other bioactive chemical) into the drip emitter per se, the herbicide or other bioactive material can be incorporated into a drip irrigation tube or tape. In any case, the bioactive chemical is incorporated into a polymer matrix which protects the bioactive chemical from chemical or biological degradation while providing a controlled but sustained release of the bioactive material to the soil adjacent the device for a substantial period of time, typically lasting many years.

The performance and life expectancy of such root growth inhibiting drip irrigation devices can be measured in terms of release rate or diffusion rate of the bioactive chemical from the host polymeric matrix in which it is bound. One of the drawbacks of present polymeric carrier delivery systems using trifluralin as a root growth inhibiting chemical is that diffusion rate or release rate of the chemical is difficult to sustain over long periods of time in a thin-walled product. That is, diffusion rate of the bioactive chemical from the host polymer is a function of the ratio of volume to surface area. For thin-walled products containing trifluralin, for example, essentially all of the trifluralin diffuses or migrates to the surface. This results in a shorter useful life of the product compared with a product of this invention in which the diffusion rate to the surface is reduced. Expected life of such thin-walled products can be extended by the present invention. Typically, products will have an increase of life expectancy of as much as 60%, so a thin-walled product of about 8 mils may increase from 5 to 8 years life, while a thicker product of 40 mils may increase from 20 to 32 years.

By way of example, with this invention drip irrigation products having a wall thickness on the order of about 8 mils, in which the impregnated bioactive chemical is trifluralin and in which the host polymer carrier is polyethylene, may have an expected life of about 20 years. (Laboratory tests can be conducted on various polymeric carrier materials containing bioactive chemicals at a certain wall thickness to estimate their stable rate of diffusion and then measure the expected life of the product.) It would be desirable to provide a long-term controlled release polymeric carrier delivery system which can extend the life expectancy of drip irrigation devices, and more particularly, to extend the useful life of thin-walled drip irrigation products by slowing the diffusion rate of bioactive chemicals such as trifluralin contained in such devices.

A more complete description of the present technology for preventing root intrusion in drip irrigation devices containing slow-release herbicides is presented in "Protection of Buried Drip Irrigation Devices from Root Intrusion through Slow-Release Herbicides," Van Vories, et al., published in the Proceedings of the Fourth International Micro-Irrigation Congress at Albury-Wadonga, Australia, Oct. 23–28, 1988. Use of similar slow-release technology in subsurface drip irrigation devices applied to waste water, irrigation and drainage systems is reported in "Sub-surface Drip Irrigation Can Reduce Pollution," R. Ruskin, Proceedings of the Irrigation and Drainage Division of the American Society of Civil Engineers, Park City, Utah, Jul. 21–23, 1993. These publications are incorporated herein by this reference.

Referring again to the Burton et al. '414 patent, and the slow-release technology disclosed in that reference, column 10, lines 10 et seq. disclose protecting a zone with 2 ppm trifluralin at 2 cm after 30 days. With the present invention adapted for drip irrigation use, intrusion of root growth in a hole approximately 2 to 2-½ mm in diameter is protected. That is, 2 ppm trifluralin protection at about 2 mm from the dripper is all that is necessary, and therefore, the present invention requires a slower release rate (compared to Burton '414) because of the smaller zone of protection.

SUMMARY OF THE INVENTION

Briefly, the invention is characterized by a slow-release product comprising a polymeric carrier, a slow-release active material dispersed in the carrier, and a fine particulate inert inorganic material dispersed in the carrier. The slow-release active material is diffusable from the carrier to produce an active function at a controllable level exterior to the polymeric carrier. The inorganic particulate material is dispersed in the resinous matrix to an extent sufficient to reduce the diffusion rate of the slow-release material to the exterior of the carrier, while the reduced diffusion rate is still sufficient to maintain an effective level of activity exterior to the carrier.

One embodiment of the invention comprises a slow-release product comprising a polymeric carrier or substrate, a slow-release material dispersed in the polymeric carrier, and an intercalation material in fine particulate form comprising an inert inorganic material having a layered structure dispersed in the polymeric carrier material. The slow-release material is dispersed between the layers of the intercalation material. The dispersed inorganic particles slow the diffusion rate of the slow-release material from the polymeric carrier.

In one embodiment, the intercalation material is a nano-clay, and the slow-release material is a bioactive material such as a herbicide to protect against root intrusion in drip irrigation applications, for example. The herbicide can comprise dinitroanaline. The bioactive material can comprise herbicides having other active functions, or alternatively, the bioactive material can comprise an insecticide that diffuses to the exterior of the polymeric carrier to produce its active function.

For drip irrigation applications in which the bioactive material is a herbicide, the slow-release product can comprise a drip irrigation emitter, or tape, or tube, or device used adjacent to an emitter to protect against root intrusion. The product also can be formed as a discontinuous bead along a drip irrigation tape, sheet or tube to protect drip emitters located in the vicinity of the beads.

In one embodiment of a drip irrigation product, an emitter made from a polymeric material containing a herbicide and the dispersed intercalation material is adapted for use in an irrigation supply tube or conduit. The supply tube can be a standard flexible plastic tubing, or it can include an inner lining containing a dispersed bactericide, as described below.

Another embodiment of the invention comprises a method for reducing the rate of diffusion of a slow-release active material through a host polymer material to increase the useful life of a slow-release product. The method comprises incorporating an intercalation material, comprising an inert fine particulate inorganic material having a layered structure, into a mixture of the slow-release bioactive material and the host polymer. The slow-release material is accommodated within spaces between the layers of the intercalation material sufficient to slow the diffusion rate of the slow-release material through the host polymer when compared with the diffusion rate of the same slow-release material through the same host polymer not containing the dispersed intercalation material.

One form of the invention comprises a drip irrigation emitter comprising a polymeric substrate base, a slow-release bioactive material dispersed in the substrate for inhibiting root growth in the vicinity of the emitter during use, and a fine particulate inorganic material dispersed in the substrate in an amount sufficient to reduce the release rate of the bioactive material from the emitter during use.

In one embodiment, the drip irrigation product includes a bactericide dispersed in the substrate in an amount sufficient to inhibit bacterial activity in the emitter during use. The bactericide can be incorporated into the dripper along with the slow-release bioactive material (herbicide). The bactericide also can be incorporated into a lining for the drip irrigation supply tube for killing slime-forming bacteria. The emitter containing the bactericide can be incorporated into drip irrigation supply tubes either of the conventional type (with no lining) or with a lining containing a bactericide.

In another embodiment, a slow-release product comprises a polymeric carrier, a slow-release active material dispersed in the polymeric carrier, and an intercalation material in fine particulate form comprising an inert inorganic material with a layered structure, in which molecules of the slow-release material are contained within the spaces between the layers of the intercalation material so as to inhibit the diffusion rate of the slow-release active material from the polymeric carrier. The intercalation material may be surface-treated to expand the spaces between the platelets that form the dispersed material. The active material is released at a controlled reduced rate, but at a level sufficient to maintain its effectiveness, while the resinous carrier maintains its structural properties.

These and other aspects of the invention will be more fully understood by referring to the following detailed description and the accompanying drawings.

DETAILED DESCRIPTION (1) Reducing the Diffusion Rate of Slow-Release Materials

One embodiment of the present invention is based on the recognition that nanometer sized inert inorganic particles, such as nanometer sized clay particles, also referred to as nano-clays, can be incorporated into a polymeric host carrier to control the diffusion rate of a dispersed slow-release material. The polymeric carrier may contain a dispersed slow-release material which diffuses to the exterior of the host carrier to produce an active function. The active slow-release material may comprise a bioactive chemical or herbicide. The presence of the nano-clay particles reduces the porosity of the polymer or otherwise obstructs the diffusion of the active material being released, thereby increasing the length of the path of the diffusion through the host polymer. This slows the rate of release of the slow-release material compared with the release rate from the same polymeric carrier having the same level of slow-release material without the added nano-clay particles.

The nanometer sized particles used to control the diffusion rate of the slow-release materials are preferably a layered clay material, also referred to as an intercalated clay material. Layered clay materials suitable for the invention include smectite clay material such as montmorillonite. Vermiculite also may be a useful layered clay material.

A presently preferred nano-clay is a montmorillonite, an alumino-silicate available from Nanocor, Inc. This material's particles are in layered form, i.e., formed as platelets. These particles measure on the order of one micron in diameter and a thickness of about 0.001 micron (or one nanometer), giving them an aspect ratio of about 1,000:1. In one embodiment, relatively small amounts of nanometer-sized clay particles approximately 2% to approximately 10% by weight are dispersed in the resinous matrix formed by the host polymer and the dispersed active material. Another nano-clay material is a hydrated aluminum silicate available under the name Closite A, from Southern Clay Products.

The use of nano-clay materials to reinforce the mechanical properties of plastic materials such as nylons and polyolefins is described in Sherman, "Nanocomposites, a Little Goes a Long Way," *Plastics Technology*, June 1999, Pages 52 to 54, incorporated herein by this reference.

The process of utilizing dispersed nano-clays for slowing the diffusion rate of the active material such as a bioactive chemical from the polymeric carrier is believed to be caused by the phenomenon known as "intercalation." Intercalation compounds are formed when the "guest" molecule, in this case trifluralin, can be accommodated in the spaces between adjacent layers of the "host" molecule, in this case the montmorillonite. Over time, trifluralin will diffuse out of the clay particles and the polymer at a rate which is slower than the release rate from a similar structure not containing the nano-clay particles. Such layered inert, inorganic fine particulate materials which are effective in controlling slow-release active materials, such as bioactive chemicals or herbicides, to slow their release rates are referred to herein as "intercalation materials." The phenomenon known as "intercalation" is described in "Preparation of inorganic—organic nanocomposites by intercalation and its application to materials," published by *Applied Chemistry*, which is incorporated herein by reference.

Slow-release products such as trifluralin which are incorporated into polymers (herein called a host polymer) such as polyethylene used as the encapsulation matrix of the prior art have been compounded by initially absorbing the trifluralin into particles of carbon black. The carbon black is used because it is inert, in particulate form, and capable of absorbing and retaining within it the trifluralin molecules similar to the absorption characteristics of a sponge. The carbon black and trifluralin preferably are absorbed at a one-to-one ratio and then blended with a small amount of polyethylene resin in particulate form. This blended material is later mixed into a standard polyethylene carrier material which can then be formed into the finished product. Alternatively, preparation of slow-release polymeric carrier materials comprising carbon filled polymers and a herbicide is described in the aforementioned Burton et al. '414 patent, particularly at column 10, lines 18–26.

Finished products would include molding the filled polymer into a drip irrigation emitter or otherwise extruding it into a tape or tubular part. It would also include extruding it as a component part of a drip irrigation supply tube, as described in part (2) below, or forming it as an add-on part for drip irrigation emitters to protect them from root intrusion.

In one embodiment of the present invention, the constituent ingredients are processed by surface-treating the nano-clay particles to form expanded spacing between the platelet layers by intercalation, absorbing the host polymeric material into the interlayer spaces to form a polymer matrix material, and mixing the carbon black/trifluralin particles with the polymeric matrix material to form the slow-release material.

Clay materials such as phyllosilicates, including montmorillonite clays, are treated with organic materials that are capable of intercalating the organic molecules between adjacent planar silicate layers of the clay material. The surface treatment increases the interlayer spacing between the adjacent silicate layers. In one embodiment, the interlayer spacing of the treated materials is from about 10 to about 100 angstroms. The surface-treated material then can be exfoliated, preferably to separate the silicate layers mechanically, such as by high shear mixing. Mixing the individual platelet particles derived from the intercalated layered silicate materials with a polymer forms a polymer matrix having such properties as enhanced film tensile strength and gas impermeability.

The clay materials of the present invention are surface treated to produce such intercalation and then exfoliated, followed by mixing the treated particles with the polymer that ultimately forms the structural component of the drip irrigation supply line or other drip irrigation component. The example below describes further processing of the polymeric matrix containing the intercalated nano-clay materials along with the carbon black/trifluralin particles to form the slow-release material.

The process for forming such intercalates is described in U.S. Pat. No. 6,057,396 to Lan et al. and U.S. Pat. No. 6,262,162 to Lan et al. Both of these disclosures are incorporated herein by this reference. These references describe the various processing techniques known to those skilled in the art that can produce the desired level of intercalation used for the clay like particles dispersed in the polymer matrix of the present invention. Other references also describing such intercalation processing are U.S. Pat. Nos. 6,251,980; 6,242,500; 6,232,388; 6,225,394; 6,124,365; and 6,107,387, also incorporated herein by reference.

Other possible embodiments of the invention may include other inert inorganic particulate materials with layered structures and with a sufficiently small particle size to incorporate molecules of a polymeric carrier material or a slow-release product between the platelet layers by intercalation activity. The dispersed intercalation material is inert in the sense that it is non-reactive, i.e., the particles to not chemically react with the polymeric matrices of the host carrier. The intercalation material is otherwise compatible with the host polymeric resinous material sufficiently to be dispersed in it and is capable of releasing the slow-release product at a controlled diffusion rate which is appreciably slower when compared with a similar resinous material not containing the intercalation particles. The slower release rate is still at a sufficient level to maintain the effectiveness of the released active material.

Other possible embodiments of materials that slow the diffusion rate by intercalation activity can include kaolin group materials such as kaolinite, silicates with layered structures, for example, biotite (a mica material), talc, apophyllite, or blends thereof. By way of example, kaolinite may be useful in certain instances where larger particle size materials may be desired, which in turn may produce a diffusion rate that is faster than using montmorillonite.

Diffusion rate can be controlled by varying the amount of intercalation materials or their various blends of particles and particle sizes.

Other embodiments of herbicides that may be useful in the present invention can include 2,6-dinitroanaline herbicides (trifluralin is within the class of dinitroanaline herbicides) and atrazine, although other slow-release materials in which their diffusion rate can be controlled by intercalation materials while present in a polymeric matrix structure can be used.

Other embodiments of the encapsulating polymeric structure in addition to low density polyethylene normally used in drip irrigation products, can include other polyolefins (polyethylene or polypropylene), high density polyethylene, polyisobutylene and its copolymers, ethylene vinyl acetate, polyvinyl chloride, nylon, thermoplastic elastomers, thermoset polymeric materials, and synthetic rubber.

The products made by this invention can be injection molded into the finished part or can be extruded into films or tubing.

(2) Process for Making Drip Irrigation Devices with Long-Term Control of Root Growth One method of applying this invention to drip irrigation is to mold a drip irrigation emitter from a material containing the slow-release herbicide and the dispersed particulate intercalation material such as the nano-clay.

Another method of applying this invention is to extrude a bead or a part of impregnated material into or onto the tube, tape or product to be protected. The impregnated part does not necessarily have to be the protected part itself but may be placed on or near the part to be protected. In this way, one may obtain a long life product from very thin-walled products and reduce the use of Treflan or other impregnated herbicide material. For example, an 8 mil tube with a 20 mil bead coextruded inside the tube can be positioned close to the emitters located on the tube.

More specifically, the invention can be carried out by extruding interrupted bead sections along the length of the sheet or tube. For example, if the drippers are to be added to the tape or tube at 12-inch intervals, separate beads approximately 2 inches long can be extruded in the vicinity of where each emitter will be placed. This can be done by a timer control on the extrusion die output to stop and start the bead extrusion process. Alternatively, the extruder die can be controlled to extrude a continuous bead which is thicker for lengths of about 2 inches at 12-inch intervals. This can be done by altering the die or motor speed during extrusion. The bead or beads are bonded by hot melt adhesion to the polymeric sheet material. The sheet material can be folded and seamed to form a tube. Alternatively, the extrusion process can be through the center of the tube directly.

In one embodiment of the invention the extruded bead or the dripper body is made from a material containing the herbicide and intercalation material described previously. Alternatively, the bead can be extruded or the dripper molded from the commonly used impregnated herbicide material without the particulate nano-clay materials added to reduce diffusion rate. In a further embodiment, the bead or dripper can contain the herbicide and a bactericide, as described below.

EXAMPLES

Four compounds were prepared which included (1) a nano-clay dispersed in a polymeric carrier, (2) a herbicide dispersed in a polymeric carrier, (3) a bactericide dispersed in a polymeric carrier, and (4) a polymeric substrate material which is moldable into a product under test after blending with the different components (1) to (3), as described below.

The nano-clay material (1) was blended into a polyethylene resin. The nano-clay material used in this example was a surface-treated montmorillonite, as described previously. (This material is also referred to herein as I30P.) In this example, 40% nano-clay is blended in a polyethylene resin. Intercalation techniques similar to those described in the Lan et al. '396 and '162 patents were used for surface treating the nano-clay particles with a surface modifier to expand the spacing between platelets. The polyethylene resin in a suitable carrier was mixed with the clay particles to form a co-intercalate material. This material was exfoliated to produce particle size reduction for component (1).

The herbicide-containing material was made of 50% polyethylene resin, 25% trifluralin, and 25% carbon black. These components were compounded into a masterbatch according to techniques disclosed in Burton et al. U.S. Pat. No. 5,116,414, for example. This herbicide-containing material is available under the mark ROOTGUARD, from Geoflow, Inc.

The bactericide component (3) comprised tributyl tin maleate dispersed in a polyolefin carrier and sold under the trademark ULTRA-FRESH, manufactured by Thompson Research Associates, Toronto, Canada.

The substrate material (4) comprised a moldable polymeric material which, in this example, comprised a linear low density polyethylene (LLDPE) resin. Other polyolefins (polyethylene and polypropylene) can be used, including high-density polyethylene, although the reduction of diffusion rate provided by this invention is not generally expected to be dependent upon the particular carrier or substrate polymeric material.

The components were blended to produce the following four sample materials used in the rate of diffusion test described below:

TABLE 1

|  | 1 | 2 | 3 | 4 |
|---|---|---|---|---|
| 130 P | 0.00 | 15.00 | 21.01 | 0.00 |
| LLDPE | 75.02 | 60.02 | 54.01 | 72.83 |
| ROOTGUARD | 24.98 | 24.98 | 24.98 | 24.25 |
| Bactericide | 0.00 | 0.00 | 0.00 | 2.91 |
| Total | 100.00 | 100.00 | 100.00 | 100.00 |

The blend was injection molded to form drippers. Four drippers in each set were placed in an aluminum foil dish and weighed. Initial weight of the drippers was 16 gm. They were then placed in an oven at 134 degrees F. (56.67 degrees C.) with a slow extraction fan to remove the trifluralin as it left the drippers. To observe the extraction rate, the samples were regularly weighed periodically over 54 days until the rate of extraction leveled off and the greatest part of the trifluralin contained in the parts had been lost.

Figure 1:
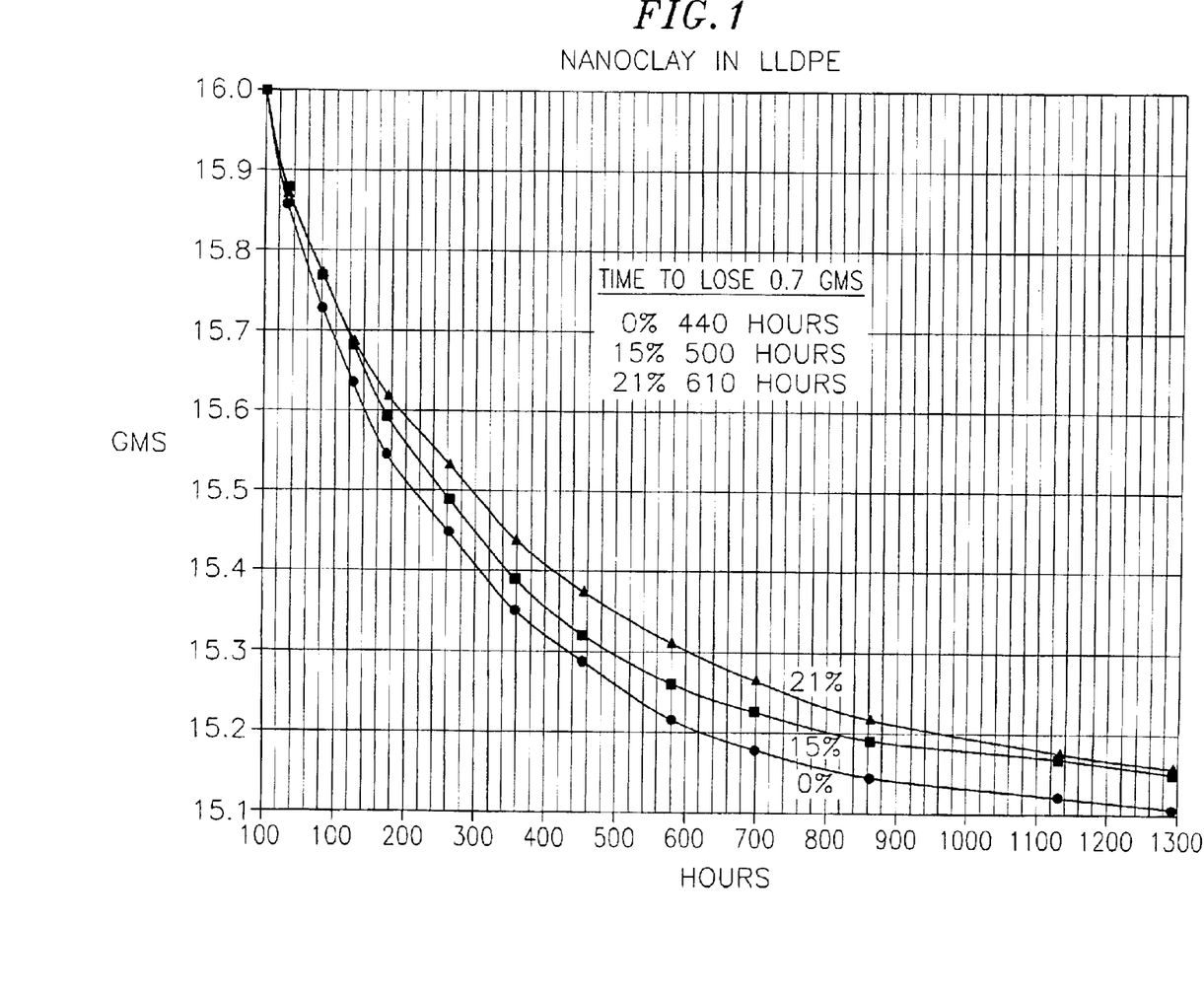
FIG. 1 is a graph illustrating the diffusion rate of a bioactive material (in this case trifluralin) from a polymeric substrate material (in this case linear low-density polyethylene), in which the diffusion rate is shown to vary in proportion to the amount of nano-clay particles contained in the substrate material, which also contains the bioactive material.

The graph shown in FIG. 1 illustrates the extraction rate of trifluralin from the drippers for the samples shown in the first three columns of Table 1. The data show that extraction rate (or release rate) of trifluralin from the drippers progressively decreases with a proportionate increase in the level of nano-clay contained in the dripper body.

More specifically, the graph of the first three columns demonstrates that a 21% concentration of IP30P (which contains 40% of nano-clay—i.e., 8.4% of the mix is nano-clay) increases the time to lose 0.7 gms of trifluralin by 38.6% ((610–440)/400)×100. The calculated initial concentration of trifluralin is 10 gms. There are unknown losses during manufacture. On the assumption that this loss is one gram then what was measured was the time to lose 77.8% of the trifluralin.

Figure 2:
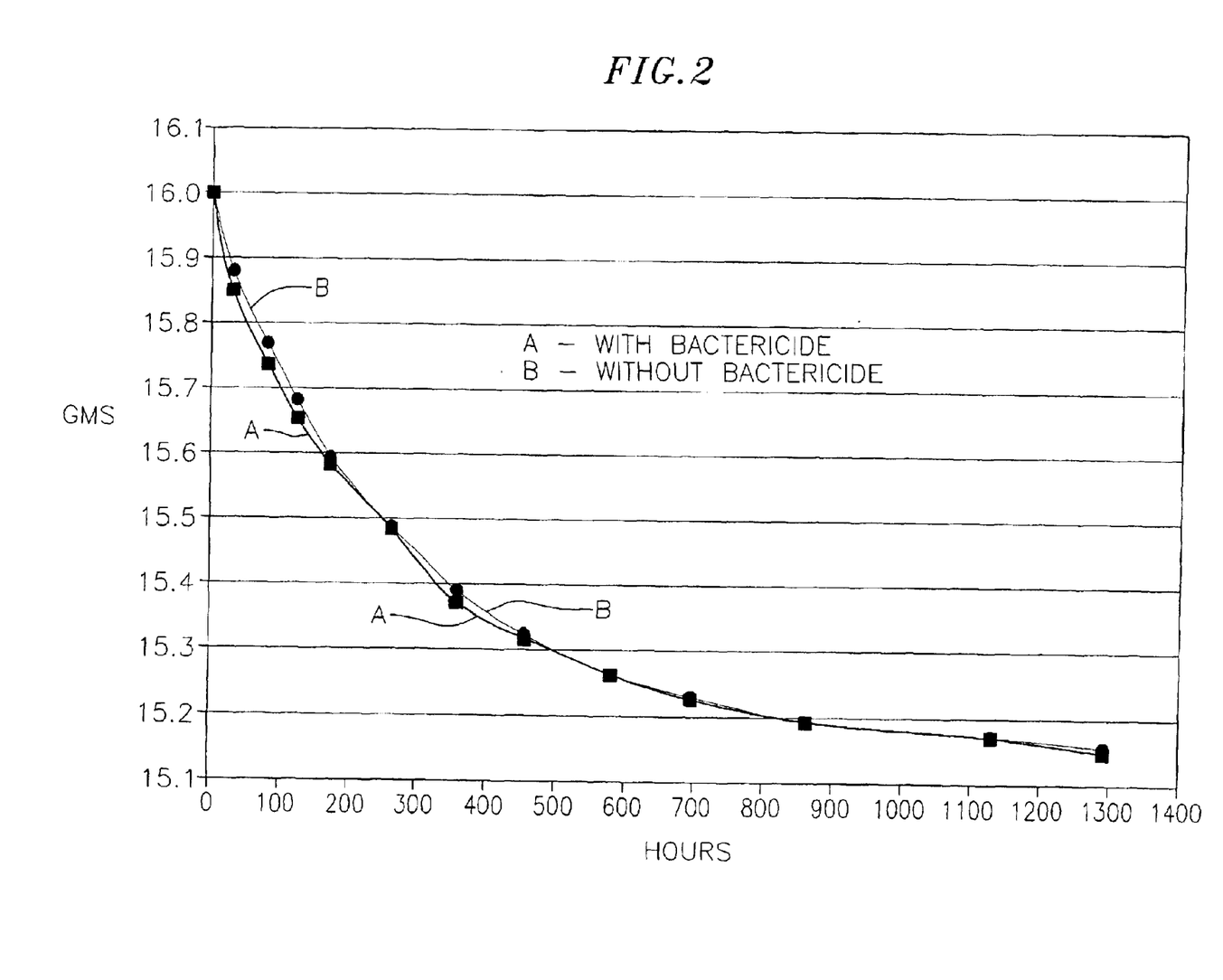
FIG. 2 is a graph showing the effect on release rate of a bioactive material from the polymeric substrate when the substrate either contains or does not contain a dispersed bactericide.
Figure 3:
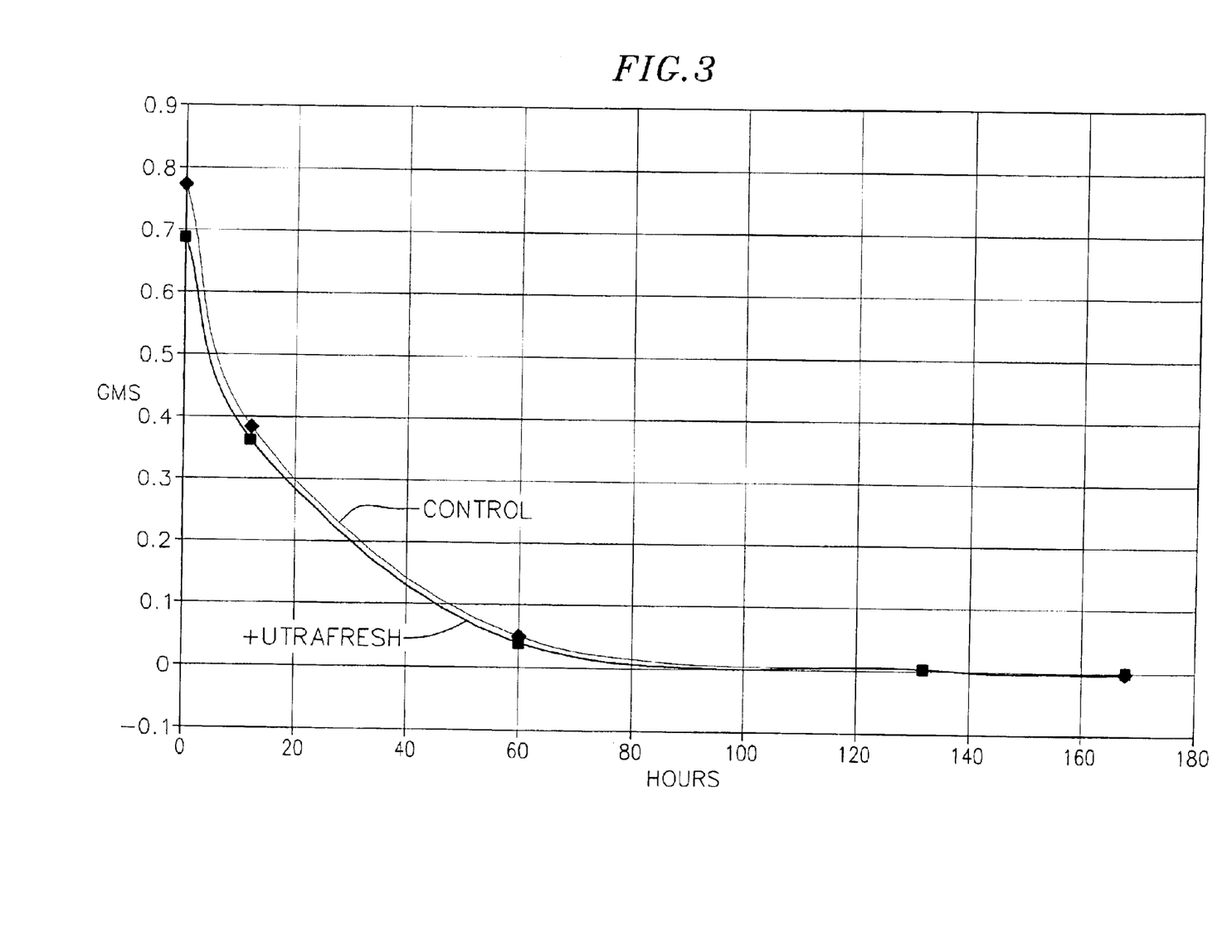
FIG. 3 is a graph showing the effect on release rate of a bioactive material from a polymeric material in which a control sample contains no bactericide and the test sample contains a bactericide, and in which both samples contain a nano-clay.

The graph shown in FIG. 2 is a comparison of release rates from the drippers of columns 1 and 4 to determine the effect of the bactericide on the release rate of the trifluralin. The graph of FIG. 3 shows a comparison of release rates from two sets of drippers in which the control did not contain a bactericide and the other set in which the control contained 3% ULTRA-FRESH bactericide. In both tests the dripper body (control) contained the nano-clay dispersion in LLDPE molded resin.

These data show that the invention is effective because:

the addition of 8.4% of a nano-clay resulted in a 38.6% increase in the time to lose approximately 78% of the trifluralin incorporated into the molded dripper. This, of course, mean that there will be an equivalent increase in the effective life; and the bactericide has no effect upon the release rate of trifluralin from the dripper.

The effectiveness of the bactericide combined with ROOTGUARD was shown in an independent test by Thompson Research Associates, the results of which are demonstrated in the table below. Four test hose samples were made containing various levels of bactericide. The test samples were treated with ULTRA-FRESH DM-9 and assessed for microbial activity (according to A.A.T.C.C. Test Method 147-1998) against the *staphylococcus aureus* organism.

TABLE 2

| Sample | Growth-Free Zone (MM)* | Contact Inhibition (%)** |
|---|---|---|
| 1. Black dripper with 0% Ultra-Fresh | 0 | 0 |
| 2. Black dripper with 0.1% Ultra-Fresh | 0 | 0 |
| 3. Black dripper with 3% Ultra-Fresh | 6 | 100 |
| 4. Tube with 6% Ultra-Fresh in green inner lining | 0 | 100 |

*The width of the growth-free zone surrounding the test specimen.
**Percentage of bacteria-free area under the test specimen.

Sample 3 of this test is similar to sample 4 of Table 1. Samples 3 and 4 demonstrated activity against the *S. aureus* organism. Samples 1 and 2 failed to show antibacterial activity. This demonstrates that 3% (2.91%) in the dripper combined with ROOTGUARD is more effective than 6% in the tube without ROOTGUARD.

FIGS. 4 through 10 illustrate various embodiments of drip irrigation products according to principles of this invention.

Figure 4:
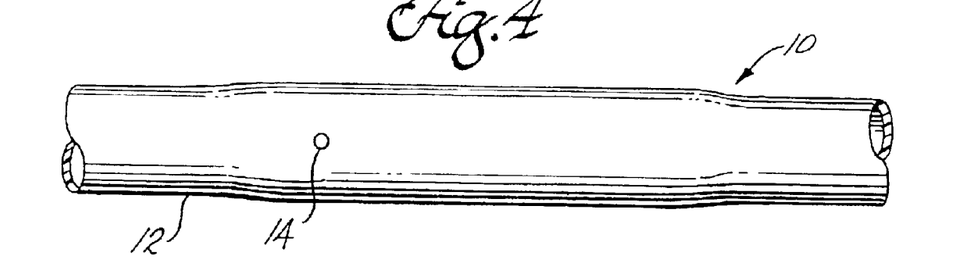
FIG. 4 is a schematic side elevational view illustrating a drip irrigation supply line containing a drip irrigation emitter.

FIG. 4 is a schematic view illustrating a supply line 10 comprised of a conduit 12 having a plurality of fluid discharge ports 14 spaced apart longitudinally along the length of the supply line.

Figure 5:
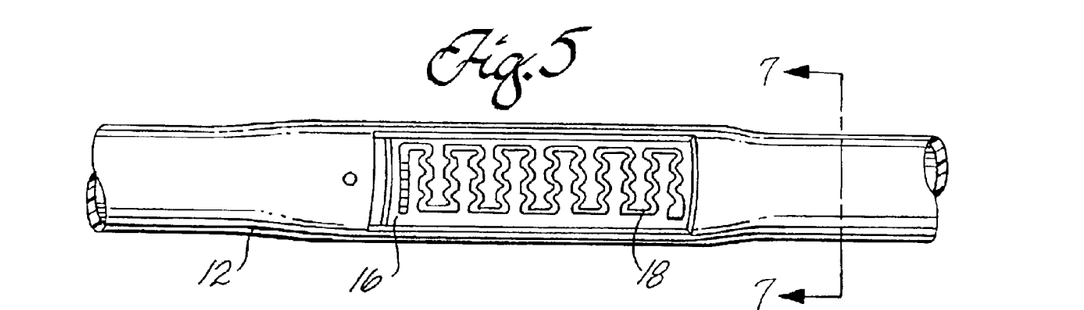
FIG. 5 is a fragmentary view illustrating the emitter within the supply line shown in FIG. 4.

FIG. 5 is a fragmentary view illustrating an emitter 16 disposed within the conduit 12.

Figure 6:
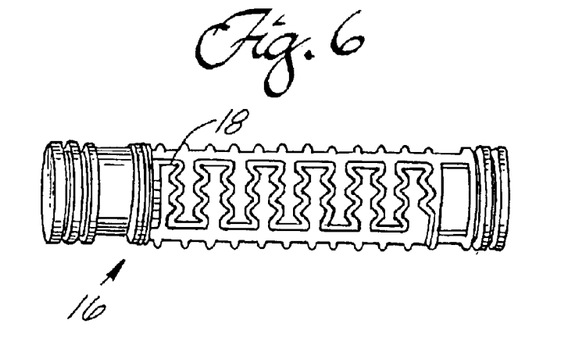
FIG. 6 is a schematic elevational view illustrating the emitter contained in the supply line.

FIG. 6 is a schematic view illustrating the emitter 16 shown in FIG. 2. The preferred embodiment uses an emitter inside the conduit. In an alternative embodiment the emitter is outside the conduit. For example, this invention may be applied to the drip irrigation system shown in U.S. Pat. No. 5,052,625 to Ruskin which discloses an emitter outside the conduit.

The emitter 16 has a water entry port (not shown) for allowing water to flow from the inside of the conduit 12 into a labyrinth 18 disposed on the outer surface of the emitter. The labyrinth 18 is a narrow passage that circuitously channels the water to generate a turbulent flow. The turbulent flow keeps fine particles in suspension. The water flows through the labyrinth 18 and out the fluid discharge port 14 and into the soil.

Figure 7:
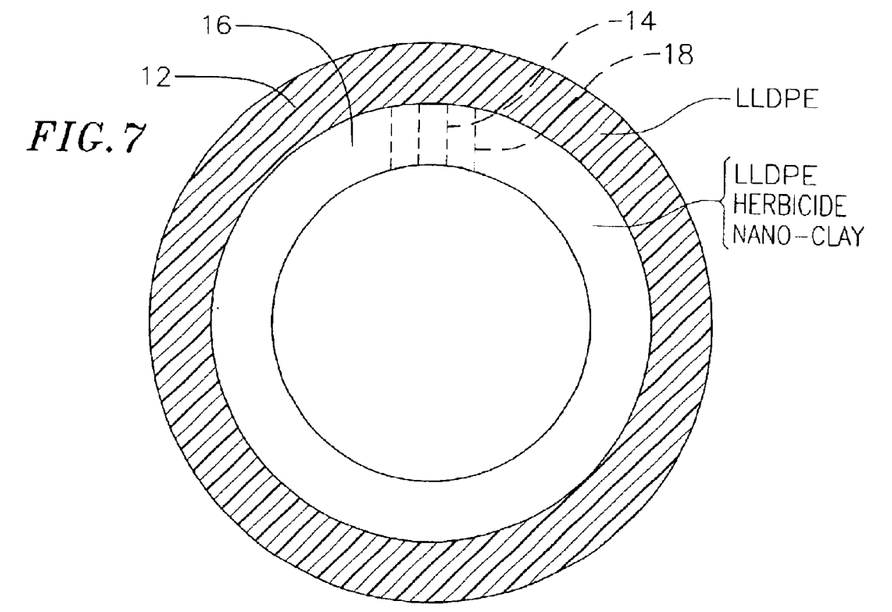
FIG. 7 is a cross-sectional view taken on line 7—7 and illustrating one embodiment of a drip irrigation device in which the emitter contains a bioactive material comprising a herbicide and a dispersed slow-release controlling particulate nano-clay material and in which the emitter is installed in a standard irrigation supply tube.

FIG. 7 illustrates one embodiment of the invention in which the emitter 16 is made from a material comprising a linear low-density polyethylene (LLDPE) which contains a dispersed herbicide such as trifluralin and a dispersed intercalation material such as a nano-clay for reducing the release rate of the herbicide during use. In this embodiment the emitter is installed in a standard flexible supply tube 12 made of linear low-density polyethylene.

Figure 8:
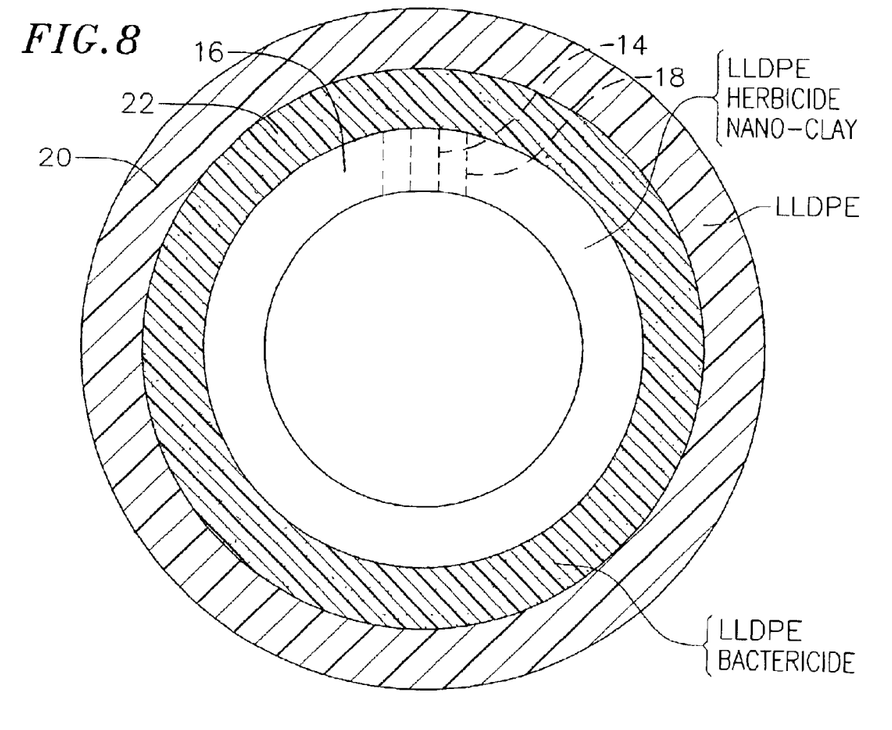
FIG. 8 is an alternative embodiment of the drip irrigation device of FIG. 7 in which the emitter is installed in a supply tube containing an inner liner having a dispersed bactericide.

FIG. 8 illustrates an alternative embodiment of the drip irrigation device shown in FIG. 7. In the FIG. 8 embodiment the drip irrigation emitter 16 is installed in a multi-layer supply line 20 having an inner liner 22 comprising a linear low-density polyethylene with a dispersed bactericide for use in killing slime-producing bacteria. One embodiment of this type of multi-layer drip irrigation conduit is disclosed in U.S. Pat. No. 5,332,160 to Ruskin which is incorporated herein by this reference.

Figure 9:
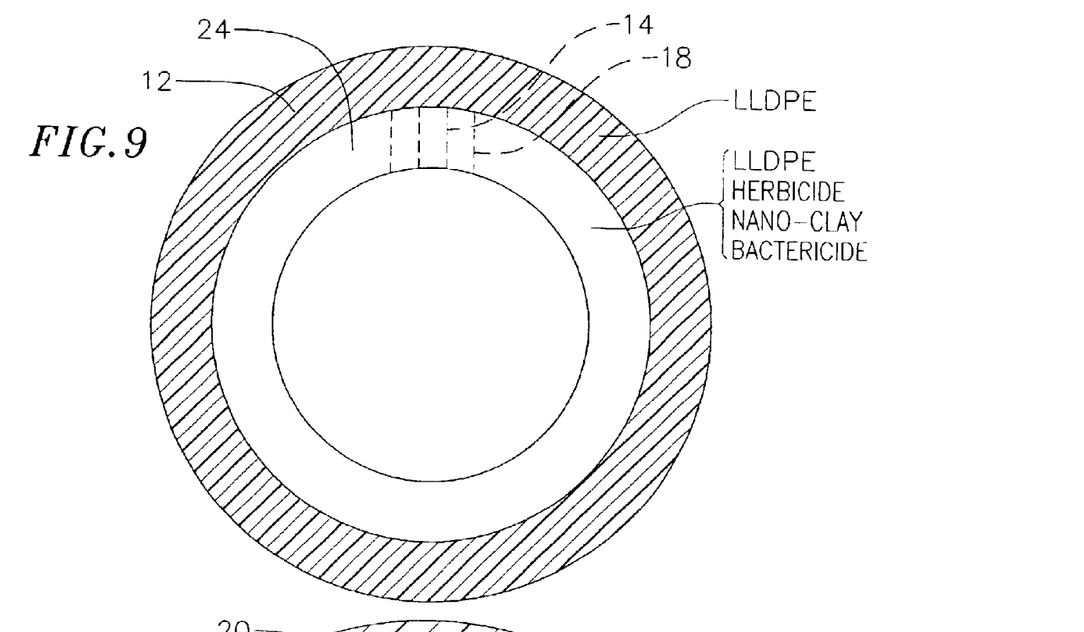
FIG. 9 is an alternative embodiment of the invention in which a drip irrigation device comprising an emitter contains a herbicide, a bactericide and a dispersed slow-release controlling particulate nano-clay material and in which the emitter is installed in a standard irrigation supply tube.

FIG. 9 illustrates an alternative embodiment of the invention in which the emitter 24 is made from a material containing a linear low-density polyethylene resin, a dispersed herbicide such as trifluralin, a dispersed nano-clay for inhibiting the release rate of the herbicide from the dripper and a dispersed bactericide for killing slime-producing bacteria in the dripper. The emitter 24 is installed in a standard flexible supply tube 12 made of linear low-density polyethylene.

Figure 10:
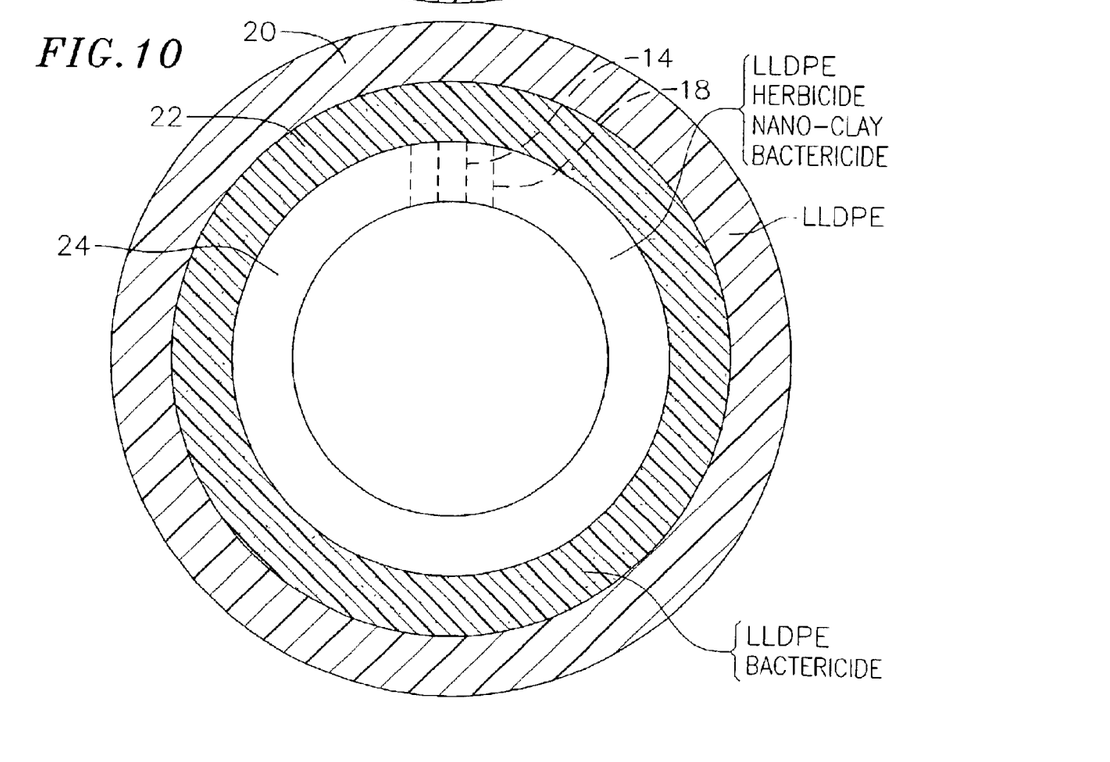
FIG. 10 is an alternative embodiment of the drip irrigation device of FIG. 9 in which the emitter is installed in a supply tube containing an inner liner having a dispersed bactericide.

FIG. 10 is an alternative embodiment of the drip irrigation device shown in FIG. 9. In the FIG. 10 embodiment the emitter 24 of FIG. 9 is installed in a multi-layer drip irrigation conduit which includes a standard outer supply tube 20 made of linear low-density polyethylene having an inner liner 22 made of linear low-density polyethylene and containing a dispersed bactericide for killing slime-forming bacteria within the supply tube.

I claim:

1. A slow-release product comprising a thermoplastic polymeric carrier, a slow-release active material which has been absorbed in a fine particulate material and dispersed in the thermoplastic polymeric carrier, and an intercalation material in fine particulate form dispersed in the carrier, the intercalation material comprising an inert inorganic material with a layered structure, in which molecules of the slow-release active material released from the particulate absorbing material are contained within spaces between the layers of the dispersed particulate intercalation material, the dispersed particulate intercalation material reducing the diffusion rate of the slow-release active material from the polymeric carrier.

2. The product according to claim 1 in which the intercalation material is a nano-clay.

3. The product according to claim 1 in which the slow-release material is a bioactive material comprising a herbicide or a pesticide.

4. The product according to claim 1 in which the intercalation material comprises montmorillonite.

5. The product according to claim 3 comprising a drip irrigation emitter, or tape, or tube, or device used adjacent to an emitter to protect against root intrusion.

6. The product according to claim 5 in which the product is formed as a discontinuous bead along a drip irrigation tape, sheet or tube to protect drip emitters located in the vicinity of the beads.

7. The product according to claim 1 in which the intercalation material comprises a layered nano-clay, and in which the slow-release active material comprises a bioactive material which has been absorbed into carbon black and then dispersed in the thermoplastic polymeric carrier.

8. The product according to claim 1 in which the particulate intercalation material is surface-treated to expand the spaces between layers.

9. The product according to claim 1 in which a bactericide is dispersed in the thermoplastic polymeric carrier.

10. The product according to claim 5 in which a bactericide is dispersed in the drip irrigation product.

11. A method for reducing the rate of diffusion of a slow-release bioactive material through a host thermoplastic polymeric material to increase the useful life of a slow-release product comprising combining an intercalation material comprising an inert fine particulate inorganic material having a layered structure with a mixture of the slow-release bioactive material which is first absorbed in a fine particulate material and then dispersed in the host polymer so that the bioactive material which is released from the absorbing material over an extended period of time is accommodated within spaces between the layers of the intercalation material sufficient to slow the rate at which the slow-release material diffuses from the host polymer when compared with the diffusion rate of the same slow-release bioactive material from the same host polymer that does not contain the dispersed intercalation material.

12. The method according to claim 11 in which the intercalation material comprises a nano-clay.

13. The method according to claim 11 in which the slow-release material is a herbicide.

14. The method according to claim 11 in which the bioactive material is first absorbed into particles of carbon black and then dispersed in the host polymer.

15. The method according to claim 11 in which the intercalation material is present in the total mixture in an amount of less than about 10% by weight.

16. The method according to claim 11 in which the particulate intercalation material is surface-treated to expand the spaces between its layers.

17. A slow-release product comprising a thermoplastic polymeric carrier, a slow-release material dispersed in the polymeric carrier, and an intercalation material in fine particulate form comprising an inert inorganic material with a layered structure in which the intercalation material has been surface-treated to expand the spacing between its platelet layers, combined with a thermoplastic polymeric carrier material absorbed into the expanded platelet layers, and exfoliated into a particulate co-intercalation material, and in which the slow-release material is dispersed in the co-intercalation material so as to inhibit the diffusion rate of the slow-release material from the thermoplastic polymeric carrier.

18. The product according to claim 17 in which the intercalation material is a nano-clay and in which the slow-release material has been absorbed into particles of carbon black dispersed in the polymeric carrier.

19. The product according to claim 18 in which the slow-release material is a herbicide or a pesticide.

20. A method for reducing the rate of diffusion of a slow-release active material through a host thermoplastic polymeric material to increase the useful life of a slow-release product comprising combining an intercalation material comprising an inert fine particulate inorganic material having a layered structure with a mixture of the slow-release material and the host polymeric material so that the dispersed inorganic material slows the diffusion rate of the slow-release active material through the host polymeric material when compared with the diffusion rate of the same slow-release material through the same host polymeric material not containing the dispersed inorganic material, in which the intercalation material has been pre-processed by surface treatment sufficient to expand the spacing between adjacent platelet layers, followed by absorbing the polymeric material into the surface-treated intercalation material to form a co-intercalate material, followed by exfoliating the co-intercalate material to separate the platelets, and then combining the resultant exfoliated co-intercalate material with the slow-release material to form a thermoplastic polymeric material having controlled slow-release properties.

21. The method according to claim 20 in which the intercalation material comprises a nano-clay and in which the slow-release material has been absorbed into particles of carbon black dispersed in the polymeric carrier.

22. The method according to claim 21 in which the slow-release material is bioactive material.

23. A drip irrigation emitter comprising a thermoplastic polymeric substrate base, a slow-release bioactive material which has been absorbed in a fine particulate material and dispersed in the substrate for inhibiting root growth in the emitter during use, and a fine particulate inorganic material dispersed in the substrate in an amount sufficient to reduce the release rate of the bioactive material from the emitter during use while the released bioactive material maintains a level of effectiveness against root growth.

24. The product according to claim 23 including a bactericide dispersed in the substrate in an amount sufficient to inhibit bacterial activity in the vicinity of the emitter during use.

25. The product according to claim 23 in which the drip irrigation emitter is installed in or on a drip irrigation supply tube.

26. The product according to claim 23 in which the fine particulate material comprises carbon black, and in which the bioactive material has been absorbed into the particles of carbon black and then dispersed in the polymeric substrate.

27. The product according to claim 26 in which the dispersed particulate inorganic material comprises a nano-clay having a layered structure.

28. The product according to claim 27 in which the nano-clay is surface-treated to expand the spacing between layers.

29. A drip irrigation emitter comprising a thermoplastic polymeric substrate base, a slow-release bioactive material dispersed in the substrate for inhibiting root growth in the vicinity of the emitter during use, a fine particulate inorganic material dispersed in the substrate in an amount to reduce the release rate of the bioactive material from the emitter, and a bactericide dispersed in the substrate in an amount sufficient to inhibit bacterial activity in the emitter during use.

30. The product according to claim 29 in which the drip irrigation emitter is installed in or on a drip irrigation supply tube.

31. The product according to claim 29 in which the bioactive material has been absorbed into particles of carbon black and then dispersed in the thermoplastic polymeric substrate.

32. A slow-release product comprising a thermoplastic polymeric carrier, a slow-release active material absorbed in a fine particulate inert material and dispersed in the polymeric carrier, and a fine particulate inert inorganic material having a layered structure dispersed in the carrier material, in which the slow-release active material is diffusable from the particulate absorbing material and through the thermoplastic polymeric carrier material to produce an active function at a controllable level exterior to the polymeric carrier, the disperse inorganic particulate material contained in the carrier to an extent sufficient to reduce the diffusion rate of the slow-release material to the exterior of the carrier while the reduced diffusion rate is still sufficient to maintain an effective level of activity exterior to the carrier.

33. The product according to claim 32 in which the active slow-release material is a bioactive material.

34. The product according to claim 33 in which the particulate inorganic material is an intercalation material comprising a nano-clay and in which the active material is absorbed into particles of carbon black.

35. The product according to claim 34 in which the polymeric carrier comprises a polyolefin material.

* * * * *

UNITED STATES PATENT AND TRADEMARK OFFICE
CERTIFICATE OF CORRECTION

PATENT NO.     : 6,821,928 B2
DATED          : November 23, 2004
INVENTOR(S)    : Ruskin

It is certified that error appears in the above-identified patent and that said Letters Patent is hereby corrected as shown below:

Column 12,
Line 34, after "material is" insert -- a --.

Column 14,
Line 1, delete "disperse" insert -- dispersed --.

Signed and Sealed this

Seventh Day of March, 2006

JON W. DUDAS
*Director of the United States Patent and Trademark Office*